(12) United States Patent
Bargh

(10) Patent No.: US 9,382,511 B2
(45) Date of Patent: Jul. 5, 2016

(54) BIOREACTOR OUTLET AIR CONDITIONING SYSTEMS AND ASSOCIATED METHODS

(71) Applicant: TAP Biosystems (PHC) Limited, Hertfordshire (GB)

(72) Inventor: Adrian Neil Bargh, Hertfordshire (GB)

(73) Assignee: TAP BIOSYSTEMS (PHC) LIMITED, Royston, Hertfordshire (GB)

( * ) Notice: Subject to any disclaimer, the term of this patent is extended or adjusted under 35 U.S.C. 154(b) by 367 days.

(21) Appl. No.: 13/660,475

(22) Filed: Oct. 25, 2012

(65) Prior Publication Data

US 2013/0288344 A1  Oct. 31, 2013

(30) Foreign Application Priority Data

Oct. 25, 2011 (GB) .................................. 1118425.6

(51) Int. Cl.
*C12M 1/34* (2006.01)
*C12M 1/02* (2006.01)
*C12M 1/00* (2006.01)
*C12M 3/00* (2006.01)
*C12M 1/12* (2006.01)

(52) U.S. Cl.
CPC ............... *C12M 41/44* (2013.01); *C12M 23/28* (2013.01); *C12M 23/44* (2013.01); *C12M 23/46* (2013.01); *C12M 23/48* (2013.01); *C12M 29/26* (2013.01); *C12M 37/02* (2013.01); *C12M 41/12* (2013.01); *C12M 41/18* (2013.01); *C12M 41/22* (2013.01)

(58) Field of Classification Search
CPC ...... C12M 23/28; C12M 41/12; C12M 23/23; C12M 23/44; C12M 23/46; C12M 23/48; C12M 29/26; C12M 41/18; C12M 41/22; C12M 41/44

USPC .............................................. 435/286.1, 289.1
See application file for complete search history.

(56) References Cited

U.S. PATENT DOCUMENTS

| | | | |
|---|---|---|---|
| 5,340,741 A * | 8/1994 | Lemonnier | ................ 435/287.4 |
| 5,424,209 A | 6/1995 | Kearney | |
| 5,443,985 A | 8/1995 | Lu et al. | |
| 5,827,944 A * | 10/1998 | Nickerson | .................... 73/23.41 |
| 5,942,022 A | 8/1999 | Bislev et al. | |

(Continued)

FOREIGN PATENT DOCUMENTS

| | | |
|---|---|---|
| DE | 202007005399 U1 | 8/2007 |
| DE | 202007005868 U1 | 8/2007 |

(Continued)

*Primary Examiner* — Michael Hobbs
*Assistant Examiner* — Liban Hassan
(74) *Attorney, Agent, or Firm* — Dickinson Wright PLLC

(57) ABSTRACT

A bioreactor outlet air conditioning system (10) has a bioreactor vessel (100) and a heat exchanger. The heat exchanger has a fluid flow path (196) from a headspace (108) in the vessel for venting air from the vessel, and a temperature control element (300) in thermal contact with the fluid flow path (196). The fluid flow path (196) may be defined by a disposable portion of the bioreactor vessel (100). A method of controlling evaporation within a bioreactor vessel (100), dependent on the required evaporation rate, adjusts the temperature of the temperature control element (300) to control the rate of evaporation of the liquid media (106) from the vessel (100), and may include monitoring fluids in the fluid flow path (196) to detect at least water content of the fluids exiting the vessel to adjust the temperature and control the rate of evaporation dependent on the detected water content levels.

15 Claims, 4 Drawing Sheets

(56) References Cited

U.S. PATENT DOCUMENTS

| | | |
|---|---|---|
| 6,432,698 B1 | 8/2002 | Gaugler et al. |
| 7,007,352 B1 | 3/2006 | Hill |
| 2009/0148941 A1* | 6/2009 | Florez et al. .................. 435/325 |
| 2010/0081577 A1* | 4/2010 | Sidhu et al. ....................... 506/7 |
| 2010/0170400 A1 | 7/2010 | van den Boogard et al. |
| 2011/0076759 A1 | 3/2011 | Reif et al. |
| 2011/0207170 A1 | 8/2011 | Niazi |
| 2011/0207218 A1 | 8/2011 | Staheli et al. |

FOREIGN PATENT DOCUMENTS

| | | |
|---|---|---|
| EP | 2251407 A1 | 11/2010 |
| EP | 2270129 A2 | 1/2011 |
| JP | 58000861 A | 1/1983 |
| JP | 62238449 A | 10/1987 |
| KR | 1020040020089 A * | 3/2009 |
| WO | 2008088379 A2 | 7/2008 |
| WO | 2011041508 A1 | 4/2011 |

* cited by examiner

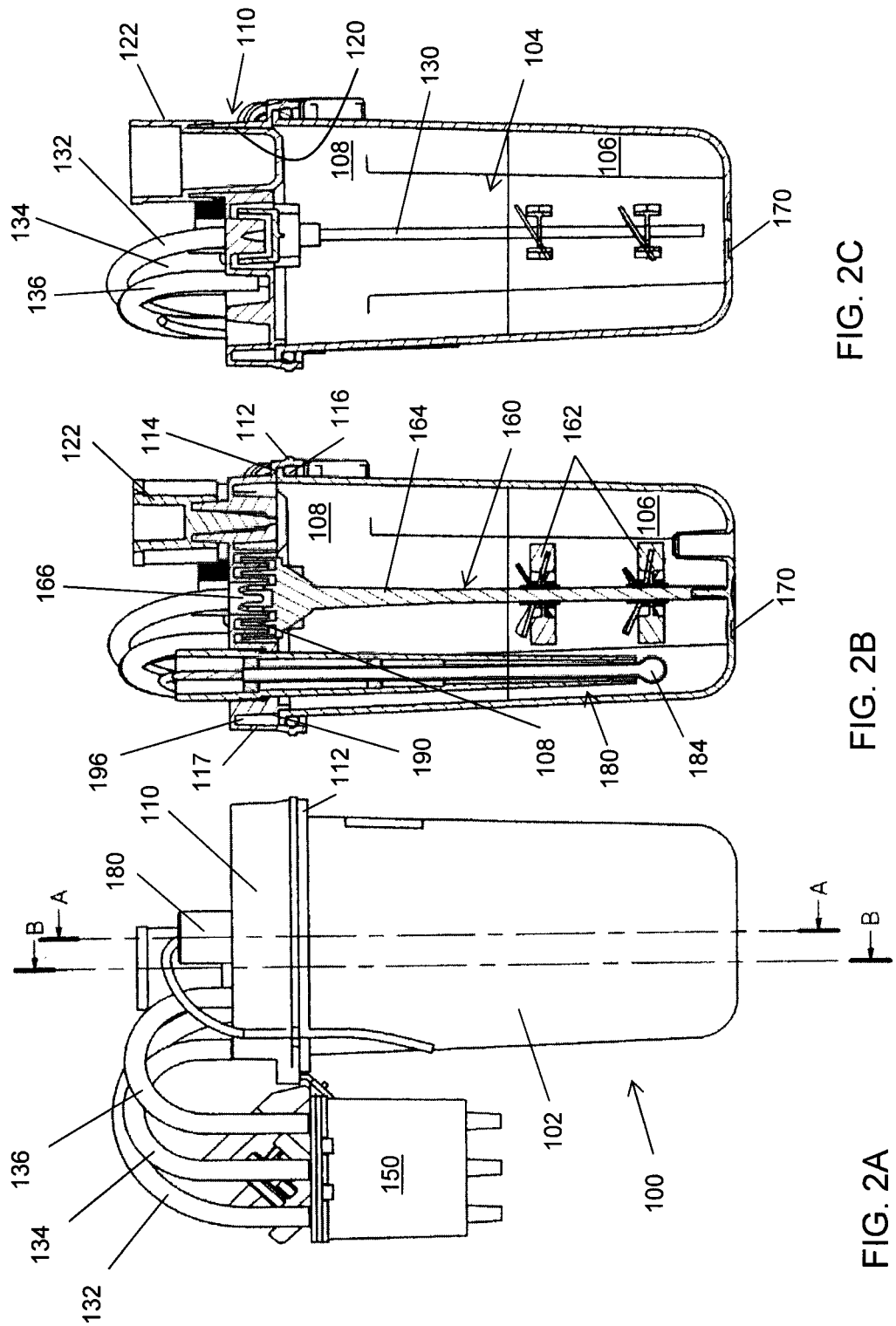

BIOREACTOR OUTLET AIR CONDITIONING SYSTEMS AND ASSOCIATED METHODS

CROSS-REFERENCE TO RELATED APPLICATION(S)

The present application claims priority to and the benefit of Great Britain Application No. 1118425.6, filed Oct. 25, 2011.

FIELD OF THE INVENTION

The invention relates generally to the field of bioreactor processing systems for cell cultures. More particularly, the invention concerns improvements to fluids management in bioreactor vessels within bioreactor systems and to associated improved methods of processing bioreactor vessels within those systems. The invention has particular application to the field of microbial culture processing, in which, for example by contrast to mammalian cell cultures, there is much greater metabolic activity.

BACKGROUND TO THE INVENTION

Cell cultures, consisting of cells growing suspended in a growth media, or on the surface of suspended particles, in solution are produced within bioreactors with careful control of a number of parameters. These bioreactors may be capable of processing large quantities of cell culture solution. For example, large-scale bioreactors can have capacities from 1-20,000 liters, or even up to 50,000 liters.

Within the bioreactor it is important to carefully control the environment to which the cells are exposed. Subtle changes in the environment can have major effects on the physiology of the cells and the amount of the target product (product titre), for example a recombinant protein, that is produced by each cell. This in turn has a major impact on the economics of the production process. The parameters that must be controlled include the concentrations of oxygen and carbon dioxide available to the cells (dissolved oxygen and $CO_2$), pH, temperature, and specific nutrient levels such as the concentration of glucose. Additionally the physical environment is critical; particularly important components including the form of the gas distribution e.g. bubble size and overall gas flow. Finally, the mixing of the liquid and cells is critical having an impact on the homogeneity within the reactor and hence the local environmental variation to which cells within a bioreactor are exposed. Such issues become significant in very large bioreactors.

A major challenge facing companies manufacturing products in bioreactor systems is the optimisation of the conditions within a bioreactor for the production of a particular product. Optimisation of conditions for a particular cell line producing a particular product can easily have magnitude level effects on the yield of the product, this in turn having a massive impact on the economics of production. Addressing this issue is not simple; there are many parameters to be controlled and the optimal approach may involve variations in these conditions over time. However, it is impractical to explore the impact of varying a range of parameters due to the lack of availability of equipment and the huge costs of operation. The actual costs of one run of a 2 l bioreactor can be over $2000. At larger scales the cost rapidly becomes prohibitive. Such issues prevent the application of modern statistical based experiment approaches to resolving the impact of multiple parameter variation typically referred to as DOE (Design of Experiment), such approaches typically requiring tens of bioreactor experiments to have value.

The opportunity for such work to have value has increased over recent years as regulatory authorities have introduced initiatives in which variations within a production run do not necessarily mean the automatic failure of a batch IF the impact of such variations in control parameters has previously been explored. This is impossible without small-scale highly parallel models of bioreactors but essential for manufacturers to remain competitive.

A further issue faced is the difficulty of selecting cell lines early in development that are robust and productive in a stirred bioreactor environment. Clearly, where high tens to hundreds of cell lines need to be screened, existing bioreactor systems are impractical.

A number of small-scale approach bioreactors have been tried, e.g. shaken multiwell plates and flasks, but these lack the ability to faithfully reproduce the conditions found in stirred, gassed systems with closed loop control of culture parameters. To date, small-scale experiment runs are generally carried out in individual bioreactors, of 1 to 10 liter capacity, containing cell cultures in solution. These are processed under careful, monitored control for a period of about two weeks. During that period, the input parameters discussed above may be varied between the individual bioreactors, with the contents of the respective bioreactors being monitored so as to determine which set of parameters achieves optimum, desired results. That set of parameters can then be used in order to scale-up the process to full production scale; the objective being to maximise cell production or cell viability, to improve production efficiency and/or to increase product titre yield.

Control of the culture parameters is required from three perspectives: i) the maintenance of a parameter at a defined set-point, within control limits, for a given time; ii) the controlled, planned variation of that parameter over time; and finally iii) the consistency and reproducibility of that parameter from bioreactor to bioreactor and run to run. Once such control is achieved, parameters can be varied and the impact of the variation on productivity determined.

As described in co-pending European patent application publication no. 2270129, from the same applicant, which describes a micro-scale bioreactor system for faithful reproduction of parameters within larger scale bioreactors, the cell culture solution within the bioreactor is stirred in order to ensure homogeneity. The rate of stirring can have a major impact on the productivity of the culture through the impact of the physical environment of the cells, for example shear, on the viability and productive life of the cells. Additionally, the stirring rate has a direct effect on mixing and therefore the efficiency of mass transfer of gasses from the input stream of bubbles into the liquid phase where it is available to the cells. The balance between stir rates and their potential negative effects and the benefits of good mixing and gas transfer must be established for a particular culture. At manufacturing scale, energy inputs to the reactor additionally become an important economic consideration.

There are two key aspects to the gas control within bioreactors: that of $CO_2$ and that of $O_2$.

The dissolved oxygen level in the bioreactor must be maintained at a set level to ensure a consistent availability to the cells such that metabolism is not limited. Typical maintenance levels vary between 15 and 50% of the maximum dissolved oxygen level achieved by air saturation. Approaches to achievement of this vary between users, some preferring to use lower input concentrations and higher flow rates, others higher input concentrations and lower flow rates. Control of the input flow rate is critical as it affects the stripping of other gases such as $CO_2$ from the culture media.

The concentration of $CO_2$ that the cells are exposed to can have significant effects on metabolism. Control of $CO_2$ is additionally used to control pH in combination with bicarbonate based buffer systems in the media. Bubbles are also a key source of damage to cells and hence control of the total gas inflow rate is an important factor in maintaining cell viability.

The pH level within the bioreactor should remain within predetermined bounds, which can vary as the cell culture develops. Generally this is achieved by a combination of a bicarbonate based buffer system within the liquid media, combined with the maintenance of a specific level of dissolved $CO_2$. However, above a certain cell density the production of lactic acid by the cells can overwhelm the buffering capability of the media and the pH is maintained within the desired limits by the addition of doses of alkali solutions to combat the increasing acidity. The addition of alkali in bioreactors is controlled as part of a feedback loop including a pH sensor.

Temperature is an important parameter within bioreactors. Generally, a heater is controlled in order to increase or decrease the amount of supplied heat. In some systems, the culture growth and energy inputs into stirring generate excess heat, so cooling and heat dissipation systems are required.

A range of nutrient feeds may be dispensed into the reactor. Typically these include media feeds which supply additional amino acids and carbon sources to replace those used in cell growth. Multiple different feeds may be added to a bioreactor on different schedules, often including pure carbon sources such as glucose. Generally, such feeds are added in response to the measurement of parameter levels within the bioreactor.

Monitoring of various parameters within the bioreactor is key to their control. Some parameters are controlled through closed loop sensing and response systems, others through sampling and off-line analysis due to the lack of appropriate on-line monitoring systems.

On-line monitoring systems are of two types: invasive and non-invasive. Invasive sensors rely on a probe carrying a sensor being inserted into the vessel and having direct contact with the culture solution. Generally, such systems are reusable and must be cleaned and calibrated between uses. Such monitors contribute to the complexity of setting up bioreactors through the requirement for disassembly from the reactor vessel for cleaning and sterilisation and the requirement for aseptic assembly. Some probes can be sterilised with the vessel but do require removal of residues and cleaning. Non-invasive sensor systems are now available in which a non-disposable sensing component has no contact with the culture, therefore does not require cleaning, sterilisation and accompanying validation of those processes.

One on-line monitoring method is to include disposable sensor spots in the vessel for remote interrogation. For example, a pH and/or dissolved oxygen sensor patches attached to the inside of the vessel can be interrogated externally; the spot is illuminated by a light source and a light detector detects emitted fluorescence, the characteristics and dynamics of which are indicative of the pH or dissolved oxygen levels within the vessel. Other techniques are available, including measurement of light diffraction and reflectance of near-infrared light. In this context, light is defined as encompassing any emission within the electromagnetic spectrum, not just visible wavelengths.

The monitoring of the vessel contents may be achieved by 'invasive' methods in which a small sample portion of the cell culture solution is removed for on-line or off-line analysis, for example via sampling port or by aspirating a sample of the solution with a pipette for dispensing for example into the sample cup of an analytical system. Likewise, a sample portion of the gases in the headspace within the vessel may be extracted for analysis in, for example, a gas analyser. That extraction may be done by a probe inserted into the headspace, or via a gas outlet port and associated conduit.

An aspect that requires monitoring and control is the liquid level within a bioreactor. During a cell culture process, liquid will evaporate from the cell culture media in a bioreactor. This is particularly the case where the cell culture is microbial, which, for example by contrast to mammalian cell cultures, has much greater metabolic activity and generally requires much high gas flow rates. The evaporated fluid will pass through the bioreactor headspace and then out through an outlet path as 'wet' air.

Often the outlet air is sampled through a gas analyser. The gas analyser may dry the air prior to measuring the $O_2$ and $CO_2$ content. Those detected parameters are useful indicators of the rate of metabolic activity in the cell culture. The water content in the air leaving the cold condenser unit is of little importance provided there is no impact on the gas analysis.

In benchtop scale systems, as shown in FIG. 4, water in the outlet air 1 is typically condensed using a condenser unit 2. Typically the condenser units 2 are either made from stainless steel or glass and have coaxial chambers, the centre 3 for the gas stream to be condensed and the outer chamber 4 to carry cold fluid. Depending on the configuration, the condensed water may run back into the bioreactor 5 or may be collected externally. The actual amount of water vapour leaving the bioreactor system is quite variable as the temperature of the bioreactor headspace 6 is not controlled nor is the actual temperature of the condenser unit 2 controlled.

In large-scale bioreactors it is usually not economical to condense the water vapour leaving the bioreactor. If required, the liquid levels may be monitored through use of liquid level sensors. The output from those sensors may used as input in a feedback loop control system to control input of replacement fluids where a drop in liquid level has been detected.

In known micro-scale bioreactor systems, this liquid evaporation aspect has either been ignored, or has been mitigated through the use of approximated algorithms to estimate expected evaporation rates; with appropriate levels of replacement fluids being input to the bioreactor.

However, in order to ensure accurate reproduction of large-scale and bench scale conditions, at micro-scale it would be beneficial to be able to control the rate of evaporation to match that experienced in a particular larger bioreactor system. Moreover, there is further benefit to being able to accurately (and reproducibly) increase or decrease the rate of evaporation from the bioreactor to determine the effects on the culture.

Accordingly, it is an object of the invention to provide a system and associated method for controlling the rate of evaporation from a bioreactor.

SUMMARY OF THE INVENTION

According to the invention, there is provided a bioreactor outlet air conditioning system comprising:
  a. a bioreactor vessel; and
  b. a heat exchanger comprising:
    i. an outlet fluid flow path from a headspace in the vessel for venting air from the vessel, wherein at least a portion of the outlet fluid flow path is an integral part of the bioreactor vessel; and
    ii. a temperature control element in separable thermal contact with at least the portion of the outlet fluid flow path that is integral with the bioreactor vessel.

The system is therefore able to adjustably control the temperature of at least that portion of the outlet fluid flow path that is integral with the bioreactor vessel. The separability of the temperature control element facilitates sterilisation because the parts in contact with the vessel contents are kept separate from the parts that control the temperature, and can therefore be removed for cleaning and sterilisation, or can be disposed of.

The system may further comprise a temperature control element in thermal contact with the bioreactor headspace. This additional temperature control element allows control of the temperature within the headspace, which can be important for example to prevent excessive condensation in the headspace, which may be a problem if it is required for water to be evaporated from the bioreactor vessel.

Optionally, the temperature control element in thermal contact with the bioreactor headspace is also the temperature control element in thermal contact with the outlet fluid flow path, such that just a single temperature control element is required both to control the temperature of the outlet fluid flow path and the temperature of the bioreactor headspace.

Typically, the bioreactor vessel comprises a body portion and a lid portion sealingly attachable thereto. At least the lid portion may be made of a disposable material, for example: a thermoplastic, such as polystyrene or polycarbonate. These are typical materials for a bioreactor vessel that is intended to be disposed of at the end of a cell culture cycle (rather than to be sterilised for re-use).

Where the vessel comprises a body portion and a lid portion, the outlet fluid flow path may be oriented in the same plane as the lid portion, in which case one convenient way to arrange the outlet fluid flow path is to form it integrally with the lid portion. The outlet fluid flow path is therefore typically in a horizontal plane in this configuration.

By having the outlet fluid flow path oriented in the same plane as the lid portion, the vertical profile of the air conditioning apparatus can be kept to a minimum. This is beneficial in terms of allowing ease of access to the vessel—particularly in the case of an automated system including a handling robot; contrast with a vertically oriented condensation coil, for example, which would impede access by the robot.

In a disposable bioreactor, the lid and body portions are typically both formed of disposable material, as above. In any event, in this embodiment it is convenient to incorporate the outlet fluid flow path into the lid portion that would be disposed of after use anyhow.

The temperature control element in thermal contact with the outlet fluid flow path (and, optionally, the headspace too), may comprise a thermally conductive block. In such an embodiment, the thermally conductive block may be in thermal contact with a separate temperature control unit that includes cooling and/or heating means. The thermally conductive block may be profiled so as to have at least one surface contiguous with at least a portion of the outlet fluid flow path.

By having the thermally conductive block and the temperature control unit as separate parts, the thermally conductive block may easily be removed from the remainder of the system, for example for sterilisation.

Profiling the thermally conductive block so as to have at least one surface contiguous with at least a portion of the outlet fluid flow path maximises the mutual surface area between the block and the outlet fluid flow path, thus maximising heat transfer between the two and resulting in most efficient condensation (or driving of evaporation) in the outlet fluid flow path.

When the outlet fluid flow path is integral with the lid portion, one convenient manner in which to profile the thermally conductive block is for the thermally conductive block to include a foot that is received within a matching groove in an upper surface of the lid portion, adjacent to the outlet fluid flow path.

Where formed integrally with the lid portion, the outlet fluid flow path may be a circumferentially arranged conduit. One convenient way to define the circumferentially arranged conduit is by the intersection of a flat lip on an upper surface of the body portion and a groove in a lower surface of the lid portion.

The circumferential arrangement of the conduit enables a maximum path to be defined in a minimum space, and enables the use of the lip on the vessel body to define the base part of the conduit.

Where the outlet fluid flow path is a circumferentially arranged conduit and the thermally conductive block includes a foot, the foot may be arcuate with the groove in which it is received being concentric with the circumferentially arranged conduit.

The system may further include a return fluid flow path for delivering fluid into the vessel. In this manner, not only can the rate of evaporation of the fluids within the vessel be controlled—for example to match those found in a larger scale bioreactor, but also the liquid level within the vessel can be controlled (again, to match a larger-scale operation).

Particularly in smaller-scale systems, the outlet fluid flow path may be defined by a disposable portion of the bioreactor vessel.

By having the outlet fluid flow path defined by a disposable portion of the bioreactor vessel, sterility of the system can easily be maintained between cell culture growth cycles. In particular, the outlet fluid flow path can be disposed of together with the disposable portion of the vessel, to be replaced by another such part for a subsequent cycle. The more expensive hardware associated with the air conditioning—i.e. the temperature control element of the heat exchanger—can be a permanent, non-disposable part of the system. This reduces the cost of running cell culture growth cycles whilst maintaining sterility and whilst enabling accurate replication of larger-scale bioreactor evaporation conditions. The entire bioreactor vessel may be disposable.

According to a second aspect of the invention, there is provided a method of controlling evaporation within a bioreactor vessel, comprising the steps of:
 a. providing a bioreactor vessel loaded with liquid media;
 b. providing a temperature control element in thermal contact with a fluid flow path from a headspace in the vessel;
 c. dependent on the required evaporation rate, adjusting the temperature of the temperature control element so as to control the rate of evaporation of the liquid media from the vessel.

This method comprises a feedback loop to control the rate of evaporation of the liquid media (e.g. cell culture) in a bioreactor, having as an output the adjustment of the temperature applied to the outlet path. One advantage of this method is that it enables an accurate replication of the conditions in a larger-scale bioreactor vessel to be carried out in a smaller-scale vessel.

The method may further include the steps of:
 d. monitoring fluids in the fluid flow path to detect at least water content of the fluids exiting the vessel; and
 e. dependent on the detected water content levels, adjusting the temperature of the temperature control element so as to control the rate of evaporation of the liquid media from the vessel.

In this manner, the feedback loop can take as an input the water content of fluids evaporated from the vessel.

The method may further include a step of:
f. dependent on the detected water content levels, adding liquid to the vessel.

By adding liquid to the vessel in dependence on the detected water content levels in the outlet fluids, the liquid level in the vessel can be maintained or adjusted.

Optionally, step f comprises returning liquid condensate from the fluid flow path to the vessel. Whereas the liquid added to the vessel may be from a separate source (of water or of other liquids) this approach provides a controllable closed loop that requires no separate liquid source.

According to a third aspect of the invention, there is provided a bioreactor system comprising: a) a disposable bioreactor vessel; and b) an outlet gas condenser comprising: i) a disposable condenser liner; and ii) a reusable element in thermal contact with the disposable condenser liner.

The temperature of the reusable element may be below, equal to, or above the temperature of the bioreactor vessel.

The reusable element may be temperature controlled. For example, the temperature of the reusable element can be set between zero degrees Centigrade and 60 degrees Centigrade.

According to a fourth aspect of the invention, there is provided a bioreactor vessel for use in any of the systems described under the first and third aspects.

BRIEF DESCRIPTION OF THE DRAWINGS

The invention will be described, by way of example, with reference to the accompanying drawings, in which:

FIG. 2A is a side elevation of a bioreactor vessel and associated filter module, for use in a system according to an aspect of the invention;

FIG. 2B is a cross-section through A-A of FIG. 2A;

FIG. 2C is a cross-section through B-B of FIG. 2A;

DETAILED DESCRIPTION

Figure 1:
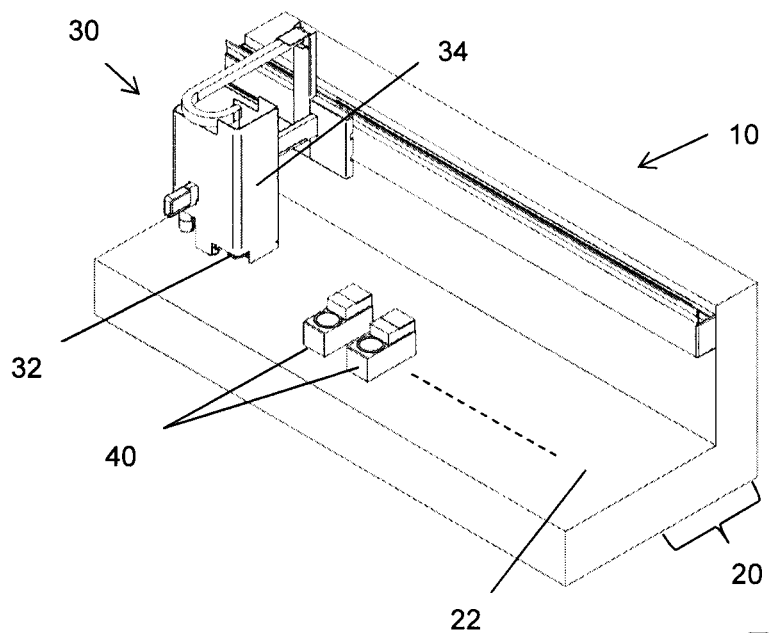
FIG. 1 is a perspective overview of an automated macro-scale bioreactor system.

An automated macro-scale bioreactor system 10 comprises, generally, a bed station 20 and a liquid handling station 30, which may be interconnected (as shown in FIG. 1) or may be separate from one another.

Figure 3:
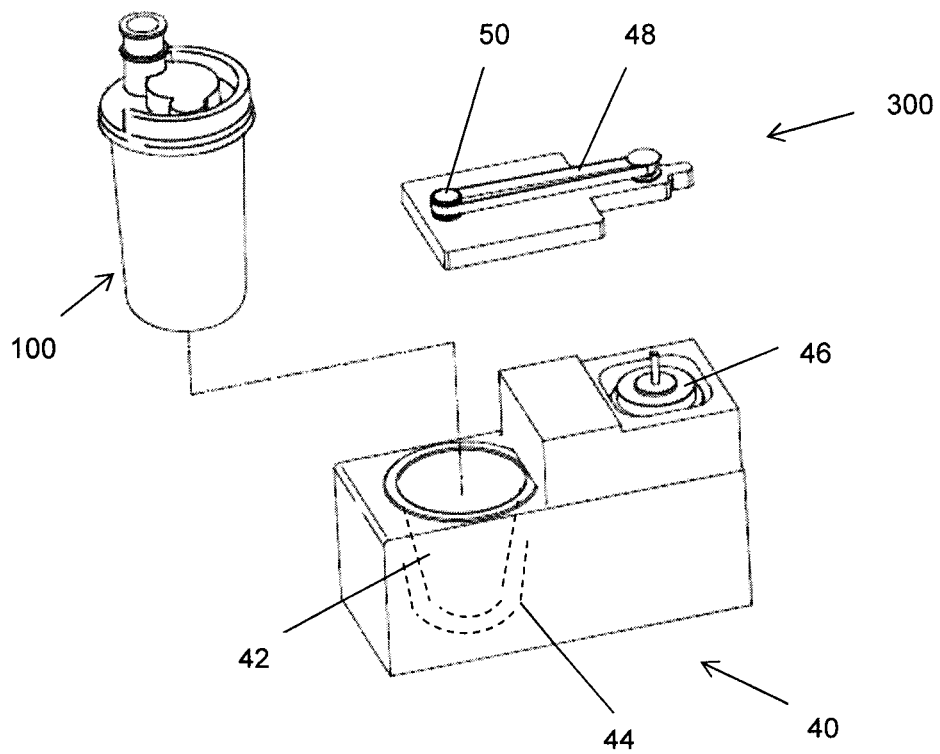
FIG. 3 is a schematic exploded view of a bioreactor module within the bioreactor system of FIG. 1.
Figure 4:
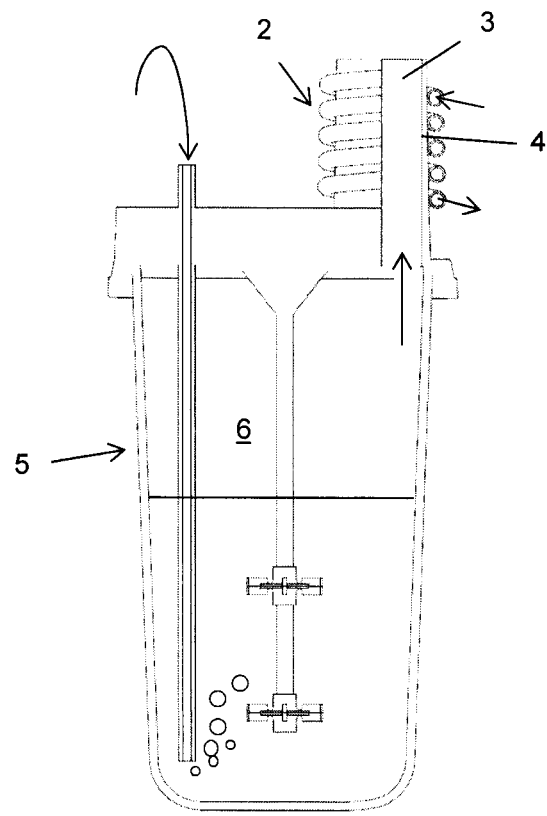
FIG. 4 is a cross-section through a known bioreactor vessel having an outlet air condensation system.

The bed station 20 comprises a platform 22 on which are mounted various modules. The modules include at least one cell culture module 40, which is described in greater detail below with reference to FIGS. 3 and 6, and, optionally, one or more further modules (not shown).

The liquid handling station 30 includes a head 32 mounted on a conventional X-Y positioning robot 34. The head 32 includes components that are selectively moveable along the Z axis. The head 32 is thus being capable of addressing and interacting with each of the modules, as will be described in greater detail below.

Each cell culture module 40 generally comprises a receiving station 42 for removably receiving a single bioreactor vessel 100. It will be appreciated, however, that the receiving station 42 could be designed to accommodate a greater number of vessels 100, with suitable adaptation.

With reference to FIGS. 2A-2C, a bioreactor vessel 100 for use with the bioreactor system 10 comprises a vessel body portion 102 defining a chamber 104 for receiving a cell culture solution 106 having a headspace 108 above. The vessel is typically a macro-scale vessel, which is to say it holds a working volume of approximately 250 ml of cell culture solution 106. It will be understood, however, that the principles described with reference to this scale of vessel may be applied, mutatis mutandis, to both larger- and smaller-scale vessels.

The vessel further comprises a lid portion 110 secured to the top of the body portion 102 by a friction fit between a skirt 112 overlapping a circumferential lip 114 on the upper edge of the vessel body portion 102. An O-ring 116 is retained between the skirt 112 and an outer wall below the lip 114 to provide a seal between the lid portion 110 and the body portion 102. The lid portion 110 includes a fluid transfer port 120, on which is removably attached a cap 122. A sparge tube 130 has a distal end opening in the cell culture solution 106 and a proximal end terminating at a port 135 through the lid portion 110. A gas input line 132 is connected at one end to the port 135 and at the other end to a fluids module 150 and may include a filter (not shown).

A stirrer 160 comprising blades 162 mounted at the base of a vertical shaft 164 is rotatably mounted within the vessel 100. The upper end of the shaft 164 includes a drive input 166, and is retained within the lid portion 110 by means of a labyrinth seal arrangement 168.

The vessel includes a DO sensor spot 170 disposed on a bottom wall of the body portion 102 to detect the DO levels of the solution 106 and to be interrogated from the exterior of the vessel 100.

A pH electrode sensor probe 180 is received in a port 182 in the lid portion 110. A distal end 184 of the electrode probe 180 extends into the vessel chamber 104 so as to be covered, in use, by the cell culture medium 106 for monitoring the pH level of the medium in a known manner.

With reference again to FIGS. 3 and 6, a temperature control element 44 is located adjacent to the vessel receiving station 42 to control the temperature of the vessel, and in particular the cell culture solution 106 in the body portion 102 within the receiving station. A motor 46 is driveable to turn a drive belt 48 and a drive element 50 that is connected to the drive input 166 by a pin 52 to transfer rotational motion to the stirrer 160.

The fluids module 150, in addition to the gas input line 132 to the sparge tube 130, includes a further gas line 136. Gas line 136 is a second input line, connected to a port 137 through the lid portion 110 for delivery of gases into the headspace 108. This input line 136 may also include a filter (not shown).

The fluids module 150 may be respectively connectable to $O_2$, $N_2$ and $CO_2$ gas supplies for selective controlled delivery of those gases, alone or in combination, to the vessel via the input lines 132 and 136.

Figure 5:
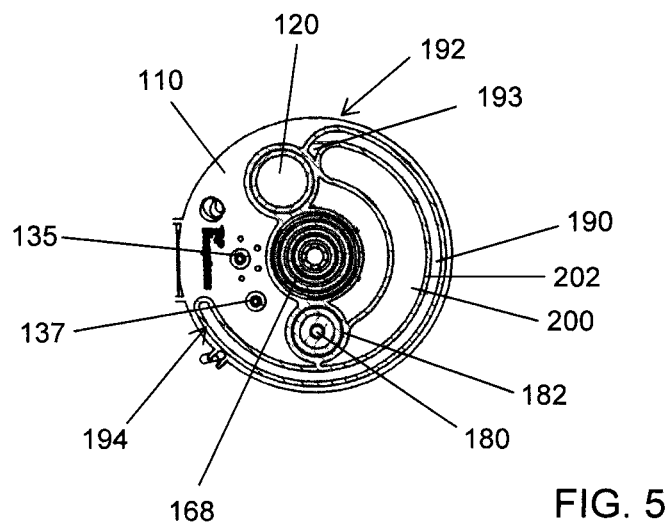
FIG. 5 is a cross-sectional plan view of a bioreactor vessel lid according to an aspect of the invention.

Referring in particular to FIG. 5, the lid portion 110 includes an arcuate groove 190 in a lower surface thereof. The groove 190 extends circumferentially around approximately 250° of the perimeter of the lid portion from a first end 192 to a second end 194. The groove 190 sits on top of a flat surface 117 on the lip 116 of the vessel body portion 102 to define a circumferentially arranged conduit 196 (see FIG. 2A). At the first end 192 of the groove, there is an enlarged opening 193 that provides a fluid communication with the vessel chamber 104 for the outlet passage of fluids evaporated from the headspace 108 into the conduit 196.

An outlet line 134 is connected at the second end 194 of the groove, for the passage of the evaporated outlet fluids to the fluids module 150. This outlet line 134 may also be provided with a filter (not shown), and is typically connected to sensors (not shown) for monitoring the gas and water content of the outlet fluid to provide an indicator of metabolic activity in the cell culture 106, as described in the introductory portion of the description.

There is a groove 200 in an upper surface of the lid portion 110, concentric with but radially inward of the circumferentially arranged conduit 196. The groove 190 and the groove 200 share a boundary wall 202.

Referring again to FIG. 6, the module 40 includes a thermally conductive block 300 having an arcuate foot 302 projecting from a bottom surface thereof. The foot 302 is sized and shaped such that its profile matches that of the groove 200 in the upper surface of the lid portion 110, and is snugly received therein. Accordingly, the contiguous surface area between the thermally conductive block 300 and the conduit 196 is maximised, for efficient transfer of heat therebetween. Likewise, the thickness of the boundary wall 202 is minimised for efficient heat transfer.

The temperature of the thermally conductive block 300 is controlled via a separate temperature control unit 310 that includes cooling and/or heating means, such as conduits filled with cold or warm flowing fluids. Heat is transferred from the temperature control unit 310 through thermal conduction at an interface 312 with the thermally conductive block 300. Having the thermally conductive block 300 and the temperature control unit 310 as separate parts means that the thermally conductive block 300 may easily be removed from the module 40, for example for sterilisation. Alternatively, the temperature control unit 310 may be integral with the thermally conductive block 300.

Figure 6:
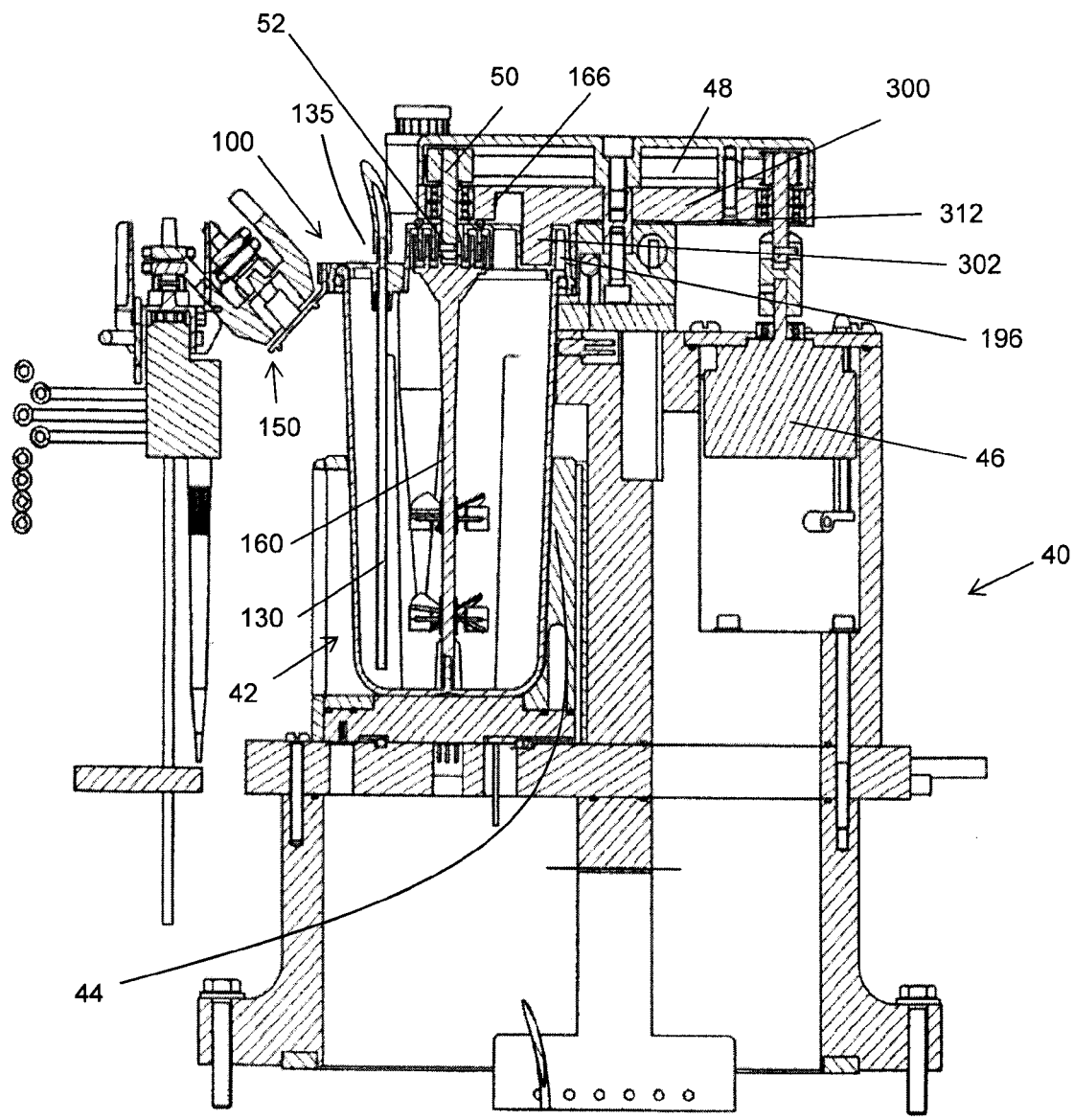
FIG. 6 is cross-section through a bioreactor module showing a bioreactor vessel in situ and with an associated air conditioning system according to an aspect of the invention attached.

The drive transfer mechanism including the drive belt 48 and the drive element 50 may be incorporated within the thermally conductive block 300, as shown in FIG. 6, or may be separate.

By controlling the temperature of the thermally conductive block 300, the temperature of the conduit 196 is controlled, which in turn controls the condensation of water in the evaporated outlet fluid within. By condensing the water in the evaporated outlet fluid within the conduit 196, the resultant water droplets return back to the vessel chamber 104 under gravity. To mitigate against the possible pooling of condensate in the bottom of the conduit 196, a wicking member (not shown) may be placed with one end in contact with the bottom of the conduit 196 and an opposite end in communication with the vessel chamber 104, thereby wicking the pooled condensate away into the vessel chamber 104.

Thus, the liquid level in the bioreactor vessel may be controlled; greater cooling of the conduit 196 resulting in greater rates of condensation and hence greater rates of return of water to the vessel, and vice versa. Furthermore, increasing the temperature of the thermally conductive block 300 will result in greater rates of evaporation, due to the greater likelihood of particulates ejected from the cell culture medium 106 into the headspace 108 being evaporated when nearing the heated block 300—particularly the foot 302 received in the groove 200 in the lid portion.

The temperature control unit 310 may receive an input signal from a sensor detecting water content in the outlet line 134, thus forming a feedback loop.

Rather than having the condensed water droplets return directly to the vessel chamber 104 as described above, an alternative arrangement would be to collect the condensed water in a separate chamber (not shown). As explained in the introduction, an objective of the invention is to replicate full-scale bioreactor conditions within benchtop scale simulations. Where the full-scale conditions to be replicated do not involve returning or replacing evaporated water to the vessel (for example to produce more concentrated cell culture material or to save on the expense of condensing the evaporated outlet fluids), then the benchtop scale simulation should not return or replace the water too (but should match the evaporation rates experienced at full scale).

In such a set-up, a return path could still be provided for the selective return of the condensate to the vessel, to enable replication of other types of full-scale bioreactor with the same benchtop apparatus.

Sometimes, it is not practical to fully replicate full-scale bioreactor processes on a smaller scale. One such situation is in the conditions for supplying nutrients to the bioreactor. At full scale, the nutrient feed may be heated, for example to enable concentrations of nutrients that would otherwise be solids or crystalline at ambient temperature to be in liquid form. Since it is not typically feasible to heat the nutrient feed in the same way for a benchtop apparatus, one way to use the benchtop apparatus to simulate full-scale bioreactor processes is to input the nutrients in a more dilute form and then to drive off the excess water content by heating the vessel contents and controlling the evaporation rate to arrive at the concentrations input to the full-scale bioreactor being replicated. Accordingly, the evaporation rate may be controlled so as to compensate for the additional water content that is initially included in such a scenario.

In benchtop scale bioreactor apparatus, the bioreactor vessels 100 are typically made of disposable materials, such as a thermoplastic, for example, polystyrene or polycarbonate. Such materials have low heat transfer coefficients and are therefore poor conductors of heat, in contrast to glass or metals, for example, that may be used to construct larger scale apparatus. It is therefore counter-intuitive to attempt to incorporate part of an air conditioning system into the disposable vessel. Nevertheless, the applicants have realised the advantages that result, including the combination of enabling accurate replication of full-scale bioreactor conditions through the application of the air conditioning to the vessel output fluids whilst ensuring ease of maintenance of sterility at minimal cost.

At its most basic, the inventive concept of the air conditioning system for a bioreactor comprises a disposable portion defining an outlet flow path, and another portion, which may or may not be disposable, in thermal contact with the outlet flow path to provide the temperature control. In one embodiment, this could be applied to a bioreactor vessel 100, disposable or not, having a disposable upstanding outlet flow tube projecting from the lid portion 102.

The temperature control element in this instance is provided by a heating/cooling jacket surrounding the upstanding outlet flow tube.

Whereas the bioreactor 100 described above has a circular plan profile, it will be understood that other shapes could instead be used. The design of the lid portion 102, and in particular the grooves 190, 200 therein may alter too. An objective of the configuration of the grooves is to provide a maximum surface area between the outlet conduit 196 and the thermally conductive block 300—particularly the foot 302 thereof—whilst ensuring ease of manufacture. The grooves 190, 200 need not be circumferential or concentrically arranged, and could instead be serpentine, with a correspondingly profiled thermally conductive block 300.

Furthermore, the path of the outlet fluids through the conduit 196 may be increased by adding features to the internal walls of the conduit, for example, resulting in a more tortuous outlet path. Such a configuration can improve in the thermal transfer between the fluids in the outlet path and the temperature control element, thereby increasing the efficiency of the system.

The invention claimed is:

1. A bioreactor outlet air conditioning system comprising:
a. a bioreactor vessel; and
b. a heat exchanger comprising:
    i. an outlet fluid flow path from a headspace in the bioreactor vessel for venting air from the bioreactor vessel, wherein a bottom portion of the outlet fluid flow path is an integral part of the bioreactor vessel;
    ii. a lid portion, wherein the outlet fluid flow path is integral with and oriented in the same plane as the lid portion;
    iii. a temperature control element in separable thermal contact with at least the portion of the outlet fluid flow path that is integral with the bioreactor vessel;
wherein the bioreactor vessel comprises a body portion configured to be attached to the lid portion, and the outlet fluid flow path is an arranged conduit defined by the intersection of an upper surface of the body portion and a lower surface of the lid portion and having an opening at a first end for fluid communication with the body portion and an opening at a second end, wherein the upper surface of the body portion forms the bottom portion of the outlet fluid flow path; and
wherein the temperature control element in thermal contact with the outlet fluid flow path comprises a thermally conductive block having a profile that is similar to a profile of at least a portion of the outlet fluid flow path so as to have at least one surface of the thermally conductive block contiguous with at least a portion of the outlet fluid flow path that is integral with the lid portion to maximize heat transfer.

2. The system of claim 1, further comprising another temperature control element in thermal contact with the bioreactor vessel headspace.

3. The system of claim 1, wherein the temperature control element is in thermal contact with both of the bioreactor vessel headspace and the outlet fluid flow path.

4. The system of claim 1, wherein the body portion is sealingly attachable to the lid portion.

5. The system of claim 4, wherein at least the lid portion is made of a disposable material.

6. The system of claim 1, wherein the thermally conductive block is in thermal contact with a separate temperature control unit that includes cooling and/or heating means.

7. The system of claim 1, wherein the thermally conductive block includes a foot that is received within a matching groove in an upper surface of the lid portion, adjacent to the outlet fluid flow path.

8. The system of claim 1, further including a return fluid flow path for delivering fluid into the bioreactor vessel.

9. The system of claim 1, wherein the outlet fluid flow path is defined by a disposable portion of the bioreactor vessel.

10. The system of claim 5, wherein the disposable material comprises at least one of a thermoplastic, polystyrene, and polycarbonate.

11. The system of claim 1, wherein the arranged conduit has a surface area, the temperature control element configured to cause a temperature change in the surface area and therefore in fluid flowing through the outlet fluid flow path.

12. The system of claim 1, wherein the outlet fluid flow path is a circumferentially arranged conduit.

13. The system of claim 12, wherein the circumferentially arranged conduit is defined by the intersection of a flat lip on the body portion and a groove in the lid portion.

14. The system of claim 12, wherein the thermally conductive block comprises a foot that is received within a matching groove in an upper surface of the lid portion, adjacent to the outlet fluid flow path, wherein the foot is arcuate and the groove in which it is received is concentric with the circumferentially arranged conduit.

15. The system of claim 12, wherein the opening at the second end of the circumferentially arranged conduit is connected to an outlet line for passage of evaporated outlet fluids from the bioreactor vessel.

* * * * *